US011087640B2

(12) United States Patent
Daniel (10) Patent No.: US 11,087,640 B2
(45) Date of Patent: Aug. 10, 2021

(54) MEDICAMENT DELIVERY TRAINING DEVICE (71) Applicant: CAREBAY EUROPE LTD, Sliema (MT)

(72) Inventor: Mattias Daniel, Täby (SE)

(73) Assignee: SHL MEDICAL AG, Zug (CH)

( * ) Notice: Subject to any disclaimer, the term of this patent is extended or adjusted under 35 U.S.C. 154(b) by 790 days.

(21) Appl. No.: 15/764,904

(22) PCT Filed: Sep. 6, 2016

(86) PCT No.: PCT/EP2016/070983
§ 371 (c)(1),
(2) Date: Mar. 30, 2018

(87) PCT Pub. No.: WO2017/060017
PCT Pub. Date: Apr. 13, 2017

(65) Prior Publication Data
US 2018/0315345 A1  Nov. 1, 2018

(30) Foreign Application Priority Data
Oct. 5, 2015 (SE) .................................... 1551277-5

(51) Int. Cl.
G09B 23/28 (2006.01)
A61M 5/20 (2006.01)
A61M 5/315 (2006.01)

(52) U.S. Cl.
CPC ......... *G09B 23/285* (2013.01); *A61M 5/2033* (2013.01); *A61M 5/3157* (2013.01);
(Continued)

(58) Field of Classification Search
CPC . G09B 23/285; A61M 5/2033; A61M 5/3157; A61M 2205/581; A61M 2005/2013
(Continued)

(56) References Cited

FOREIGN PATENT DOCUMENTS

WO  2011/123024 A1  10/2011
WO  2012/076494 A1  6/2012
(Continued)

OTHER PUBLICATIONS

International Search Report and Written Opinion for Int. App. No. PCT/EP2016/070983, dated Nov. 9, 2016.

*Primary Examiner* — Jerry-Daryl Fletcher
*Assistant Examiner* — Jennifer L Korb
(74) *Attorney, Agent, or Firm* — McDonnell Boehnen Hulbert & Berghoff LLP (57) ABSTRACT The present disclosure relates to a medicament delivery training device comprising a body, a needle cover, a rotator that is torsionally biased, and a plunger rod. When the needle cover is moved from an extended position to a retracted position relative to the body, this linear motion is transformed into a rotational motion of the rotator which thereby releases the plunger rod. The plunger rod, which is biased, is thereby able to move axially. During axial motion of the plunger rod, the plunger rod is arranged to engage with the rotator to thereby displace the rotator axially, eventually resulting in a first angular distance rotation of the rotator. Upon release of the biased needle cover from the extended position, the rotator is allowed to rotate a second angular distance, thus obtaining a position which prevents the needle cover to move from the extended position towards the retracted position.

20 Claims, 8 Drawing Sheets (52) U.S. Cl.
CPC ............... *A61M 2005/2013* (2013.01); *A61M 2205/581* (2013.01)

(58) Field of Classification Search
USPC .......................................................... 434/262
See application file for complete search history.

(56) References Cited

FOREIGN PATENT DOCUMENTS

| | | | | |
|---|---|---|---|---|
| WO | 2014/095424 A1 | 6/2014 | | |
| WO | WO-2014095424 A1 * | 6/2014 | .......... | A61M 5/3146 |
| WO | 2015/110327 A1 | 7/2015 | | |

* cited by examiner

MEDICAMENT DELIVERY TRAINING DEVICE

CROSS REFERENCE TO RELATED APPLICATIONS

The present application is a U.S. National Phase Application pursuant to 35 U.S.C. § 371 of International Application No. PCT/EP2016/070983 filed Sep. 6, 2016, which claims priority to Swedish Patent Application No. 1551277-5 filed Oct. 5, 2015. The entire disclosure contents of these applications are herewith incorporated by reference into the present application.

TECHNICAL FIELD

The present disclosure generally relates to a medical device. In particular, it relates to a medicament delivery training device for provide medicament delivery training to a user.

BACKGROUND

Medicament delivery devices such as auto-injectors and inhalers nowadays provide possibilities for the users themselves to handle medicament delivery in an easy, safe and reliable manner. Moreover, such devices also facilitate the administration of drugs for hospital personnel.

The MOLLY® auto-injector is an example of an auto-injector currently on the market. The general principles of structure and operation of the MOLLY® auto-injector are disclosed in WO 2011/123024 A1. WO 2011/123024 A1 discloses a medicament delivery device comprising a drive means configured to act on a medicament container for expelling a medicament, a holding means configured to hold the drive means in a pre-tensioned state, an activation means configured to interact with the holding means for releasing the drive means from the pre-tensioned state. The device further comprises feedback means configured to interact both with the holding means and with the drive means for generating an audible and/or tactile and/or visual signal indicating that the medicament has been completely expelled. The MOLLY® auto-injector provides audible signal feedback indicating that a medicament has been completely expelled. This is particularly advantageous when administering a medicament into an area of the body where the user has difficulties or cannot see the amount that been administered, for example when administering a drug into the buttocks area.

Before a user commences a drug administration programme by means of an auto-injector, it may be valuable for the user to undergo training to learn how to administer a drug properly by means of a particular auto-injector. A training device may be used for this purpose, of which an example is disclosed in WO 2012/076494 A1. However, this disclosure does not provide a training mechanism with audible signal feedback to indicate that the medicament has been completely expelled.

SUMMARY

In view of the above, a general object of the present disclosure is to provide a medicament delivery training device that provides a user with audible signal feedback during drug administration training.

There is hence provided a medicament delivery training device comprising a body, a torsionally biased rotator received by the body, which rotator is torsionally biased in a first rotational direction, and which rotator is rotatable between a default rotator position and a final rotator position, an axially biased plunger rod received by the rotator, wherein in the default rotator position the rotator is axially locked, and engaged with the plunger rod to prevent axial movement of the plunger rod, a needle cover received by the body, axially movable and rotationally fixed relative to the body, which needle cover is movable between an extended position relative to the body and a retracted position, and which needle cover is biased towards the extended position, wherein the needle cover is arranged to rotate the rotator in a second rotational direction opposite to the first rotational direction during movement of the needle cover from the extended position to the retracted position, to thereby release the rotator from being axially locked and release the plunger rod from engagement with the rotator and thereby enable axial movement of the plunger rod, and wherein during axial movement the plunger rod is arranged to engage with the rotator to thereby displace the rotator axially, and to allow rotation of the rotator in the first rotational direction, wherein the rotator is arranged to rotate a first angular distance, limited by the needle cover, in the first rotational direction during axial movement of the rotator, and wherein the rotator is arranged to rotate a second angular distance in the first rotational direction, into the final rotator position during return motion of the needle cover to the extended position to allow engagement with the needle cover, and thereby enable locking of the needle cover in the extended position.

In connection with the plunger rod being released from engagement with the rotator, a first audible signal in the form of a click is provided as the plunger rod is pushed towards the proximal end of the body due to its biased state. This first audible signal provides feedback to the user that the medicament administration has commenced, i.e. that the plunger rod has been set in linear motion. A first audible signal indicating the commencement of drug administration is also a feature of the MOLLY® auto-injector.

As the rotator reaches a temporary stationary state after having been allowed to rotate a first angular distance, a second audible signal is provided. This indicates that the medicament administration is completed. This second audible signal provides feedback to the user that the medicament administration has been completed and corresponds to a similar audible signal of a MOLLY® auto-injector indicating that the medicament has been completely expelled.

Lockout of the needle cover in the extended position upon finalised administration is also provided in the same manner as for the MOLLY® auto-injector.

Thus, in view of the above, an effect which may be obtainable by means of the medicament delivery training device is that it provides the same experience in use as a MOLLY® auto-injector or an auto-injector similar to the MOLLY® auto-injector. Since the medicament delivery training device mimics the MOLLY® auto-injector, a user may learn how to properly administer medicament with a MOLLY® auto-injector or any other similar auto-injector.

One embodiment comprises a syringe dummy, wherein in the default rotator position of the rotator, the syringe dummy is arranged to prevent the rotator from axial movement. The syringe dummy may hence provide the initial axial locking of the rotator.

According to one embodiment each of the syringe dummy and the rotator has a respective radial member arranged to abut each other in the default rotator position of the rotator.

Linear movement of the rotator towards the proximal end of the body can thereby be prevented.

One embodiment comprises a biased wedge member received by the plunger rod, which plunger rod has a heel arrangement protruding radially in opposite directions, wherein the wedge member is arranged to press the heel arrangement towards the inner surface of the syringe dummy. Friction between the syringe dummy and the plunger rod, in particular between a plunger and the syringe dummy, may thereby be provided. The linear motion of the plunger rod may therefore be slowed down and kept essentially constant, thus mimicking the expulsion of medicament of an auto-injector.

According to one embodiment the wedge member is biased towards a proximal end of the body.

One embodiment comprises a removable cap having a rod arranged to be received by the needle cover and arranged to reset the medicament delivery training device, wherein during insertion into the body the rod is arranged to move the plunger rod from a final plunger rod position in which the rotator is in the final rotator position to an initial plunger rod position.

According to one embodiment, during movement of the plunger rod towards the initial plunger rod position, the plunger rod is arranged to guide the rotator into a position in which the rotator is allowed to rotate in the first rotational direction into the default rotator position.

The medicament delivery training device may thereby be reset into its initial state prior to drug administration for further training.

According to one embodiment the plunger rod is rotationally locked relative to the body.

According to one embodiment the plunger rod and the rotator have a first guide arrangement which allows rotation of the rotator relative to the plunger rod and axial movement of the plunger rod relative to the rotator.

According to one embodiment the first guide arrangement comprises a groove that includes an axial groove portion and one tangential groove portion at each end of the axial groove portion, and a rib arranged to engage with the groove, wherein one of the plunger rod and the rotator is provided with the groove and the other one of the plunger rod and the rotator is provided with the rib.

According to one embodiment the rotator and the needle cover have a second guide arrangement which enables rotation of the rotator and which enables locking of the needle cover in the extended position.

According to one embodiment the second guide arrangement includes two guide surfaces and a pin member arranged to be guided by the two guide surfaces, wherein one of the rotator and the needle cover is provided with the two guide surfaces and the other one of the rotator and the needle cover is provided with the pin member.

One embodiment comprises an end cap, wherein the end cap has a radially protruding member and the rotator has a distal end cut-out, wherein the radially protruding member is arranged in the distal end cut-out in the default rotator position of the rotator, and wherein the radially protruding member is arranged to abut the distal end of the rotator, outside the distal end cut-out, in the final rotator position, to prevent axial movement of the rotator. Thus, axial movement of the rotator, in particular towards the distal end of the body may thereby be prevented and the needle cover may therefore be locked out in the extended position upon its return to the extended position.

According to one embodiment the rotator has a heel which in the final rotator position is arranged to prevent the needle cover to move from the extended position to the retracted position.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The medicament delivery training device disclosed herein can be utilised for training a user to administer medicament with an auto-injector similar in structure and function as the present medicament delivery training device.

The medicament delivery training device comprises a body, a rotator, a plunger rod rotationally fixed relative to the body, and a needle cover that is rotationally fixed relative to the body. The rotator is torsionally biased, and each of the plunger rod and the needle cover are biased axially. In an initial state of the medicament delivery training device, the rotator is engaged with the plunger rod to thereby prevent axial movement of the biased plunger rod. Moreover, in the initial state, the rotator is axially locked.

The needle cover is arranged to be actuated between an extended position and a retracted position relative to the body. The needle cover is biased towards the extended position. The needle cover is arranged to interact with the rotator. Linear movement of the needle cover is for example transformed into a rotational motion of the rotator. During linear motion, from the extended position to the retracted position, the needle cover is arranged to rotate the rotator to thereby release the plunger rod from engagement with the rotator and to enable axial movement of the rotator. The plunger rod may as a result due to its biased state move axially towards the proximal end of the body, mimicking a drug administration procedure.

When the plunger rod has moved a first distance axially, it is arranged to engage with the rotator to thereby displace the rotator axially. Upon this engagement, the plunger rod allows a certain rotation of the rotator.

When the plunger rod and the rotator have moved a second distance axially concurrently, the needle cover allows the rotator to rotate a first angular distance, which results in an audible signal, namely the second audible signal described above. Upon release of the needle cover, it returns to the extended position, and during this linear motion, the rotator is allowed to rotate a second angular distance, into a final rotator position, to thereby enable engagement with the needle cover. The needle cover may thereby be locked out in the extended position. In this final state, a removable cap having a rod, may be utilised to manually push the plunger rod back to its initial position, whereby the rotator is rotated and set in its default rotator position. The medicament delivery training device may thereby be reset for further training.

An example of a medicament delivery device will now be described in more detail with reference to FIGS. 1-5*d*.

Figure 1:
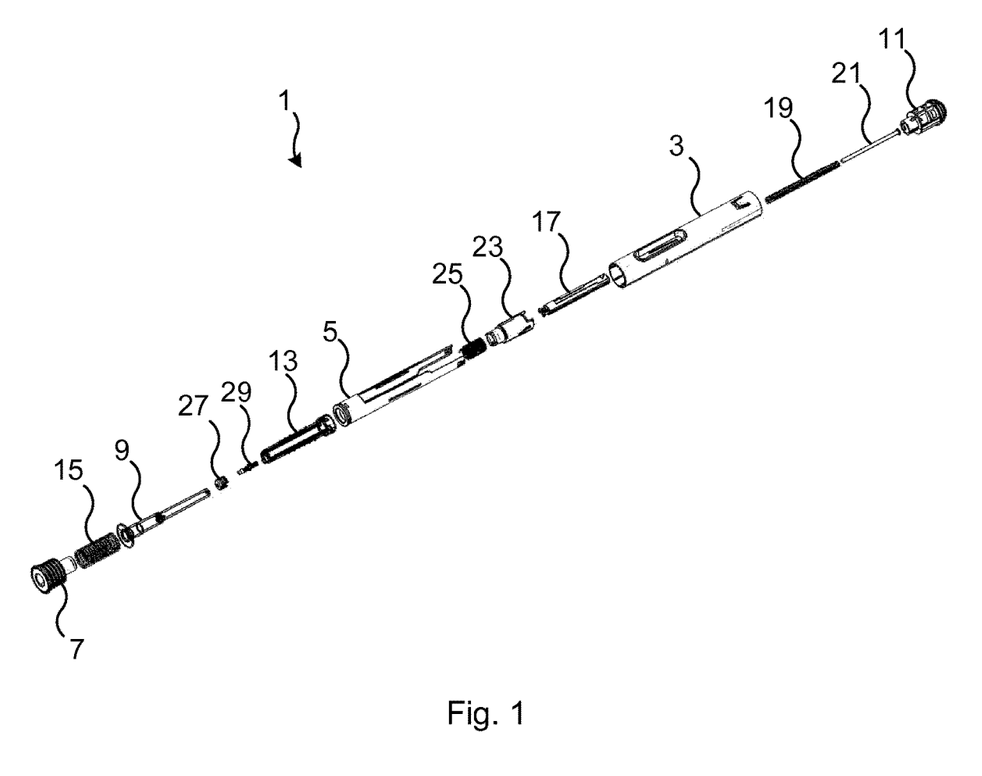
FIG. 1 is an exploded view of an example of a medicament delivery training device.

FIG. 1 shows an example of a medicament delivery training device 1. The medicament delivery training device 1 comprises a body 3, a needle cover 5 arranged to be received by the body 3, a removable cap 7, a rod 9 that is mountable to the cap 7, a rear cap 11, a syringe dummy 13, a first biasing member 15, e.g. a spring, arranged to bias the needle cover 5 axially, a plunger rod 17, a second biasing member 19, e.g. a spring, arranged to bias the plunger rod 17 axially, a guide rod 21 arranged to be received by the second biasing member 19, a rotator 23 arranged to receive the plunger rod 17, which rotator 23 is tubular and arranged to interact with the plunger rod 17 and with the needle cover 5, a torsional biasing member 25, e.g. a torsion spring, arranged to torsionally bias the rotator 23, a plunger 27 arranged to be mounted at the proximal end of the plunger rod 17, and which may in a sense be seen to form part of the plunger rod in a mounted state, and a wedge member 29 arranged to be biased by the second biasing member 19 and which wedge member 29 is arranged to press a proximal end portion of the plunger rod 17 radially outwards.

FIGS. 2*a*-2*d* show different states of the medicament delivery training device 1; prior to use, during use, and during manual resetting.

Figure 2A:
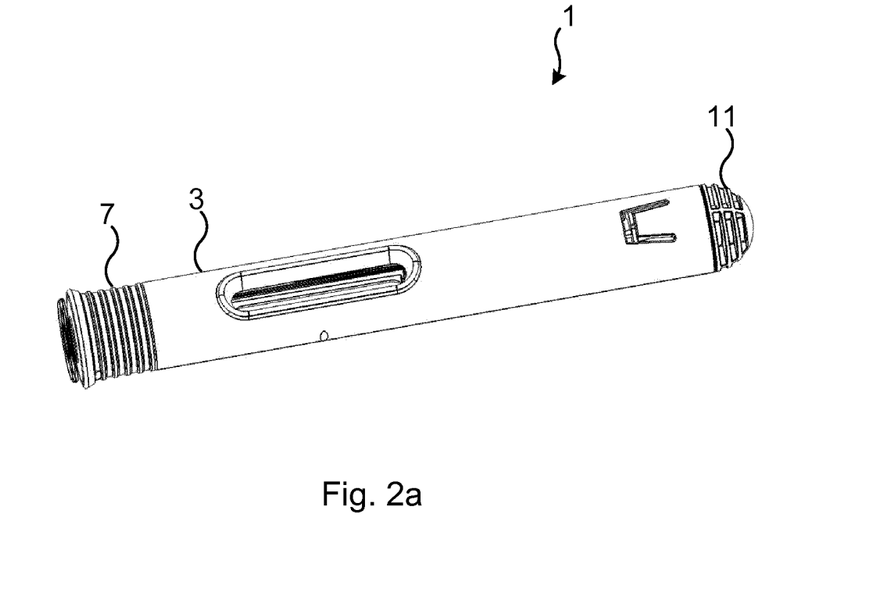
FIG. 2a depicts the medicament delivery training device in FIG. 1 in an initial state.

FIG. 2*a* shows a perspective view of the medicament delivery training device 1 in an initial state. In the initial state, the medicament delivery training device 1 is ready to be used for training purposes.

Figure 2B:
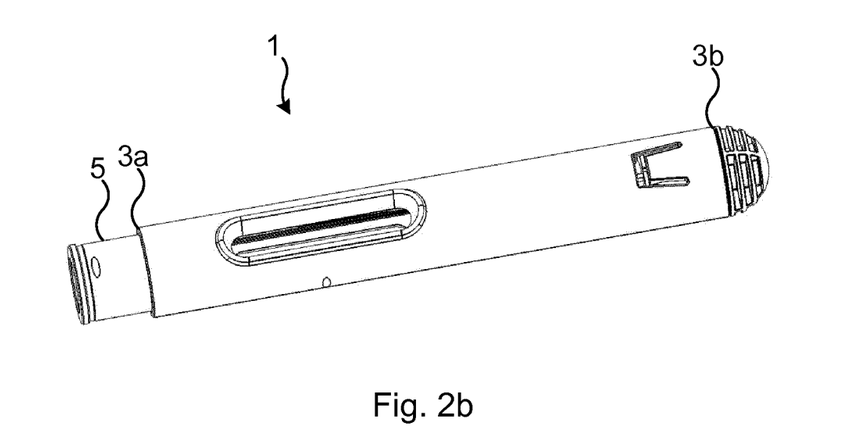
FIG. 2b shows a perspective view of the medicament delivery training device in FIG. 1 in a the initial state with the cap removed.

FIG. 2*b* shows a perspective view of the medicament delivery training device 1 in the initial state with the removable cap 7 removed. The needle cover 5 is arranged to be moved between an extended position relative to the body 3, shown in FIG. 1*b*, and a retracted position relative to the body 3, shown in FIG. 2*c*. The needle cover 5 is biased towards the extended position. Thus, in the initial state, the needle cover 5 is in the extended position.

The body 3, which forms a housing of the medicament delivery training device 1, has a proximal end 3*a* and a distal end 3*b*. The proximal end 1*a* is that end of the medicament delivery device 1 at which cap 7 can be mounted and the distal end 1*b* is the opposite end, i.e. the end where the end cap 11 is located.

Figure 2C:
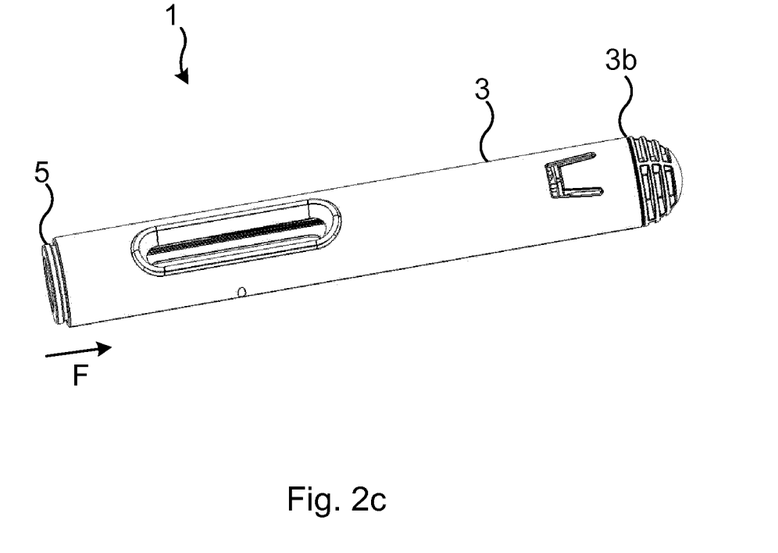
FIG. 2c shows a perspective view of the medicament delivery training device in FIG. 1 in an activated state.

In FIG. 2*c*, the medicament delivery training device 1 is in an activated state in which the needle cover 5 has reached its retracted position and the plunger rod 17 has been released from its engagement with the rotator 23. The needle cover 5 may be moved towards the retracted position by applying a force F onto the needle cover 5, directed towards the distal end 3*b* of the body 3. This force F is normally obtained by pressing the distal end of the medicament delivery training device 1 towards a training surface such as the area of the body where drug administration would be performed with an auto-injector upon the completion of the training programme. The plunger rod 17 is in this state moved axially due to its biased state, to thereby mimic medicament expulsion.

Figure 2D:
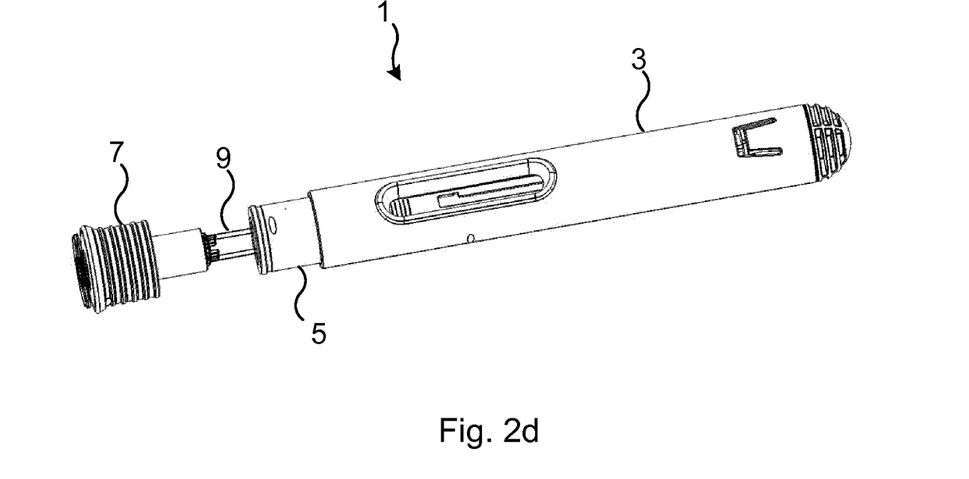
FIG. 2d shows a perspective view of the medicament delivery training device in FIG. 1 in a state in which it is reset to the initial state.

In FIG. 2*d* the needle cover 5 has been returned to its extended position and it is locked out in this position after the mimicking of drug administration has been completed. In order to reset the medicament delivery training device 1 to enable further training, the removable cover 7, including the rod 9 is inserted by a user into the proximal end of the medicament delivery training device 1. The rod 9 is pushed manually by the user such that it moves axially inwards into the body 3 and is received by the syringe dummy 13. The plunger rod 17 which in this state is inside the syringe dummy 13 may thereby be pushed towards the distal end 3*b* of the body 3 into the initial plunger rod position. During this linear motion, the plunger rod 17 actuates the rotator 23 such that the rotator 23 is set into its default rotator position. To this end, the medicament delivery training device 1 is ready for a new administration procedure.

Figure 3A:
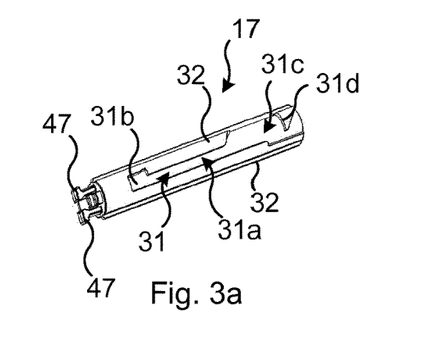
FIG. 3a shows a perspective view of an example of a plunger rod.
Figure 3B:
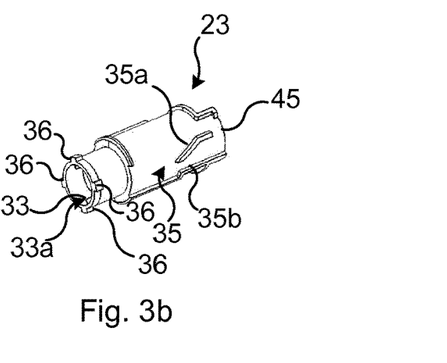
FIG. 3b shows a perspective view of an example of a rotator.

FIG. 3*a* shows a perspective view of an example of a plunger rod 17 and FIG. 3*b* depicts an example of a rotator 23. The plunger rod 17 and the rotator 23 have a first guide arrangement 31, 33 which allows rotation and axial movement of the rotator 23 relative to the plunger rod 17. The first guide arrangement 31, 33 comprises a groove 31 that includes an axial groove portion 31*a* and one tangential groove portion 31*b*, 31*c* at each end of the axial groove portion 31*a*, and a rib 33*a* arranged to engage with the groove 31. According to the present example the plunger rod 17 is provided with the groove 31 and arranged on the external surface of the plunger rod 17 and the rotator 23 is provided with the rib 33*a*, arranged on the inside surface of the rotator 23. The tangential groove portion 31*b* allows for rotational motion of the rotator 23 when the rib 33*a* is positioned in the tangential groove portion 31*a*. Moreover, the tangential groove portion 31*c* also allows for rotational motion of the rotator 23, when the rib 33*a* is positioned in the tangential groove portion 31*c*. The groove 31 is delimited by a distal end wall 31*d* which is arranged to engage with the rotator 23, in particular with the rib 33*a* when the plunger rod 17 has been displaced a sufficient axial distance.

As an alternative to the above, it would also be possible to implement the groove on the inside surface of the rotator and the rib on the external surface of the plunger rod.

Figure 3C:
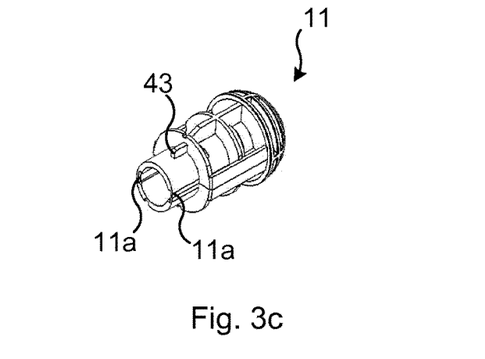
FIG. 3c shows a perspective view of a example of an end cap.

The plunger rod 17 is arranged with means for preventing rotation relative to the body 3. The plunger rod 17 may be arranged to be engaged with the end cap 11 to thereby prevent rotation relative to the body 3. Hereto, the end cap 11 may be arranged to be engaged to the body 3 to rotationally lock the end cap 11 relative to the body 3. The plunger rod 17 may for example be provided with axial ribs 32 extending along the external surface of the plunger rod 17. As shown in FIG. 3e, the end cap 11 may be provided with corresponding axial grooves 11a in which the axial ribs 32 are arranged to slide to thereby allow axial displacement of the plunger rod 17. Alternatively, the plunger rod could be provided with axial grooves and the end cap could be provided with axial ribs.

Figure 3D:
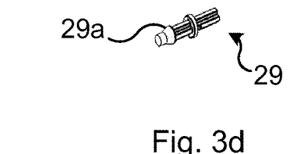
FIG. 3d shows a perspective view of a wedge member.
Figure 3E:
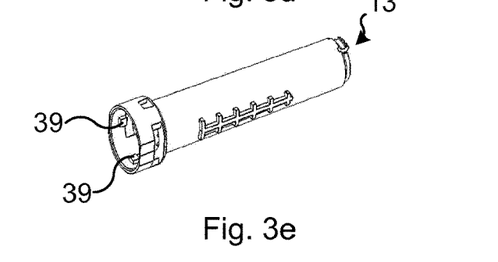
FIG. 3e shows a perspective view of a syringe dummy.
Figure 3F:
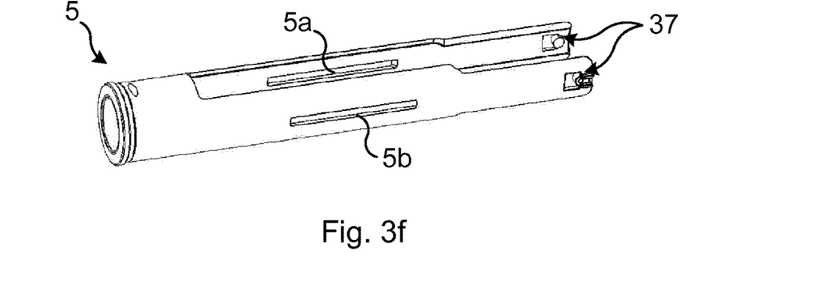
FIG. 3f shows a perspective view of a needle cover.

The rotator 23 and the needle cover 5 have a second guide arrangement 35, 37, as shown in FIGS. 3b and 3f, which enables rotation of the rotator 23 and which enables locking of the needle cover 5 in the extended position upon being released from the retracted position. The second guide arrangement 35, 37 includes two guide surfaces 35a, 35b and a pin member 37 arranged to be guided by the two guide surfaces 35a, 35b. According to the present example the rotator 23 is provided with the two guide surfaces 35a, 35b and the needle cover 5 is provided with the pin member(s) 37.

The needle cover 5 is arranged to be rotationally locked to the body 3. This may for example be implemented by means of axial needle cover grooves 5a, 5b extending along the external surface of the needle cover 5, and corresponding axial ribs provided on the inner surface of the body 3 engaging with the axial needle cover grooves 5a, 5b. Alternatively, the needle cover could be provided with external axial ribs and the body could be provided with corresponding internal axial grooves.

The rotator 23 is arranged to be axially locked in the default rotator position which is obtained prior to movement of the needle cover 5 from the extended position to the retracted position, when the medicament delivery training device 1 has been reset, and is in the initial state. The rotator 23 may in the default rotator position be axially locked by the syringe dummy 13. The proximal end of the rotator 23 may for example be provided with one or more external radial tabs 36 arranged on the external surface of the rotator 23. The distal end of the syringe dummy 13 may be provided with internal radial tabs 39 arranged on the inner surface of the syringe dummy 13. In the default rotator position, the external radial tabs 36 of the rotator 23 may be aligned axially with the internal radial tabs 39 of the syringe dummy 13. Upon rotation of the rotator 23 by means of the needle cover 5, this alignment may be removed, whereby the rotator 23 is enabled to be displaced axially.

The rotator 23 furthermore has a distal end cut-out 41. The end cap 11 has a radially protruding member 43. The radially protruding member 43 is arranged in the distal end cut-out 41 in the default rotator position of the rotator 23. The radially protruding member 43 is arranged to abut the distal end 45 of the rotator 23, outside the distal end cut-out 41, in the final rotator position. Further axial movement of the rotator 23 may thereby be prevented. As a result, both the plunger rod 17 and the rotator 23 are prevented from further axial displacement.

FIG. 3d shows an example of the wedge member 29. The wedge member 29 is arranged to be received by the plunger rod 17 and biased by the same first biasing member 19 as the plunger rod 17. The plunger rod 17 has a heel arrangement 47 protruding radially in opposite directions. The wedge member 29 is arranged to press the heel arrangement 47 towards the inner surface of the syringe dummy 13. The wedge member 29 may therefore have a wedge-shaped proximal end portion 29a tapering in a direction towards the proximal end of the wedge member 29. The wedge-shaped proximal end portion 29a pushes the heel arrangement 47, which may be realised in the form of tabs, radially outwards. The heel arrangement 47 may be arranged to be received by the plunger 27, which may have a flexible, rubbery structure, which bears against and pushes towards the inner surface of the syringe dummy 13 due to the radial force applied by the biased wedge member 29 to the plunger rod 17. This results in friction between the syringe dummy 13 and the plunger 29. A controlled, slowed down and even plunger rod motion may thereby be provided.

With reference to FIGS. 4a-5e, the operation of the medicament delivery training device 1 will now be described in more detail.

Figure 4B:
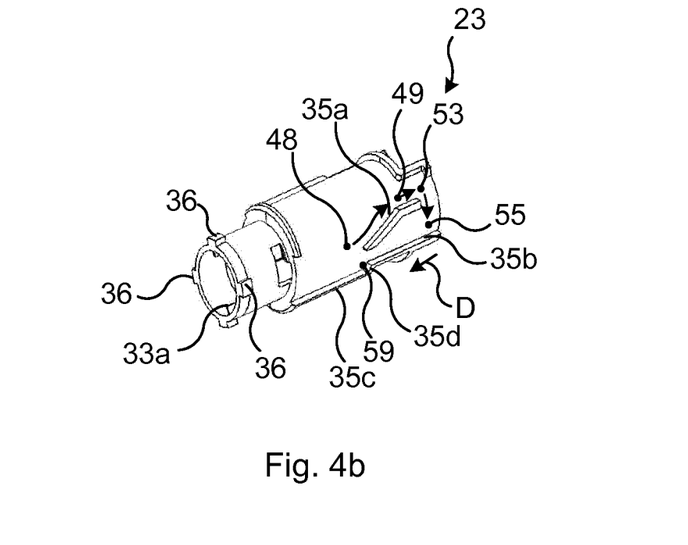
Figure 5A:
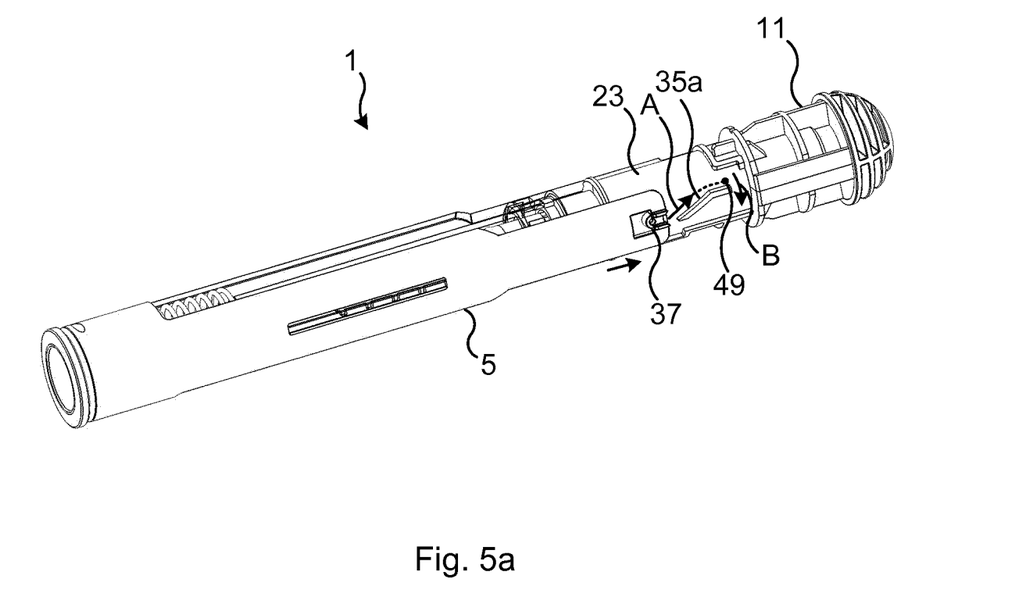
FIGS. 5a-e show the medicament delivery training device in use with the body removed to illustrate the interaction between internal components.

FIG. 5a shows the medicament delivery training device 1 in the initial state, without the body 3, in order to better illustrate the interaction between the internal components. The needle cover 5 is in the extended position. The pin member 37 is essentially axially aligned with the lower portion of the guide surface 35a of the rotator 23. The guide surface 35a, a first guide surface or a first cam surface, is inclined and may have a linear slope. This inclination provides for the rotation of the rotator 23 upon linear motion of the needle cover 5. The pin member 37 will move as shown by arrow A during linear motion towards the retracted position, while arrow B shows the resulting rotation of the rotator 23. Only the rotator 23 will in this case rotate, since the needle cover 5 is rotatably fixed to the body 3. The pin member 37 is moved to the position 49, to obtain the retracted position, along the first guide surface 35a, which corresponds to linear motion only of the needle cover 5 due to the rotation of the rotator 23. This is also illustrated in FIG. 4b, where reference number 48 indicates the start position of the pin member 37, in the extended position of the needle cover 5, and in FIG. 5b. As previously explained, the external radial tabs 36 of the rotator 23 are rotated and are thereby no longer in alignment with the internal radial tabs 39 of the syringe dummy 13. The rotator 23 is thus enabled to move axially.

Figure 5B:
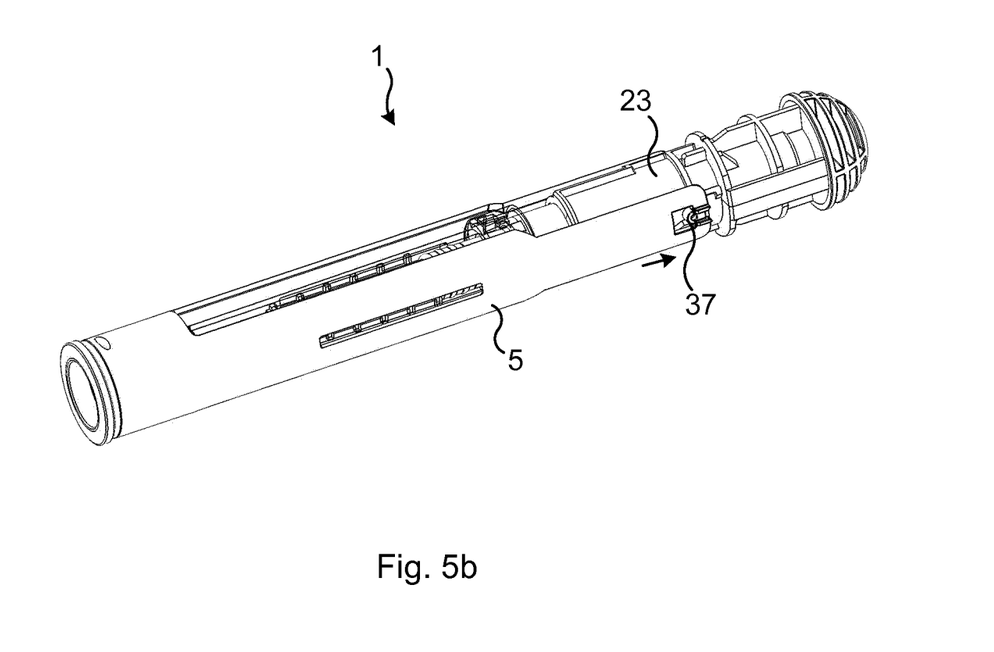

In FIG. 5b, the medicament delivery training device is shown in the activated state, in which the needle cover 5 is in the retracted position. This corresponds to the position 49 shown in FIGS. 4b and 5a.

Figure 4A:
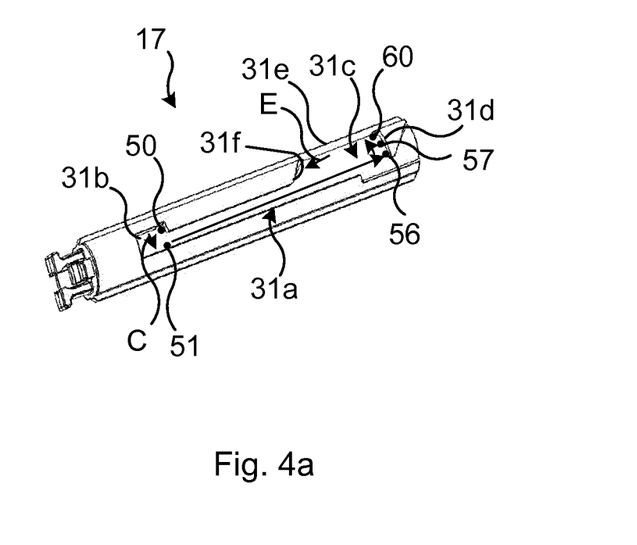
FIGS. 4a-b depict the plunger rod and rotator with arrows to show the interaction during use.
Figure 5C:
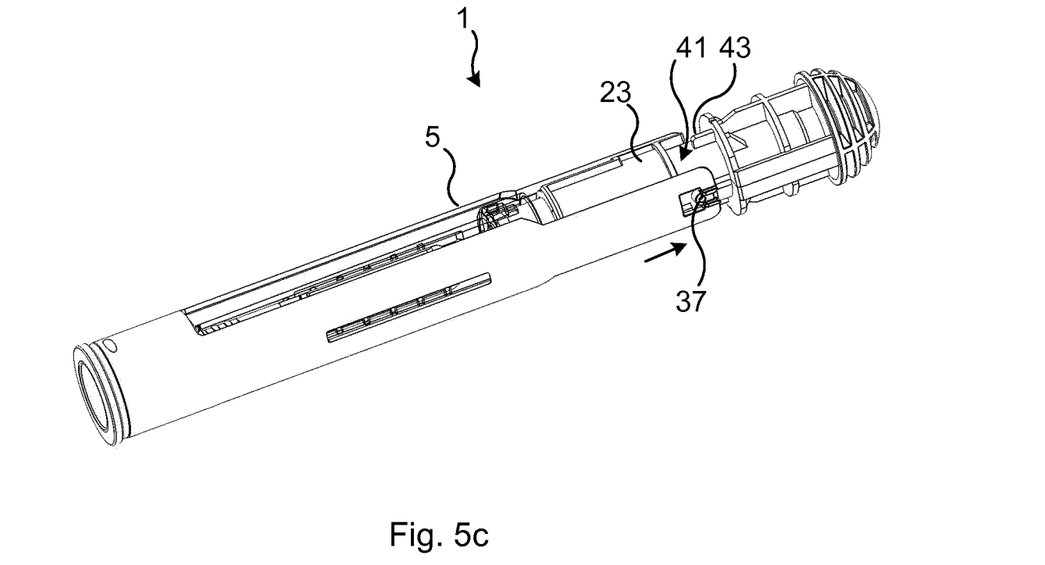
Figure 5D:
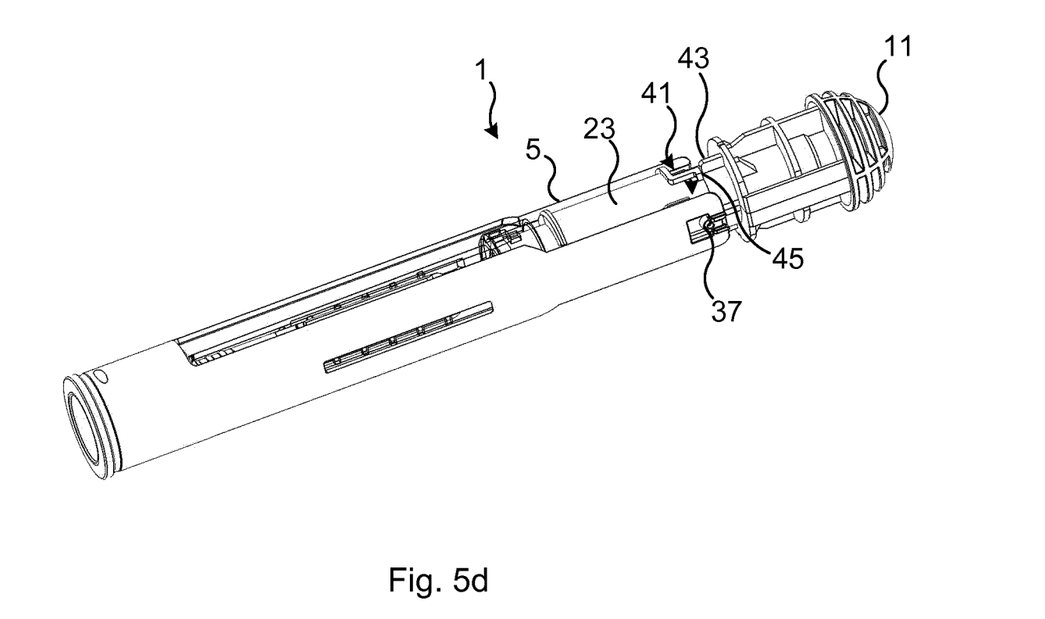

Turning now to FIG. 4a, the interaction between the plunger rod 17 and the rotator 23 during this movement of the needle cover 5 will now be explained. The rotator 23 is torsionally biased in a first rotational direction. During the above-explained rotation shown by means of arrow B, the rotator 23 rotates in a second rotational direction opposite to the first rotational direction. The rotator 23 thereby rotates relative to plunger rod 17, and the rib 33a is rotated according to arrow C in FIG. 4a such that it becomes positioned in the axial groove portion 31a in position 51. The plunger rod 17 is thereby released from engagement with the rotator 23, and is displaced axially due to its biased state. The plunger rod 17 will thereby move axially and eventually engage with the rotator 23. This engagement is obtained when the rib 33a reaches the distal end wall 31d of the groove 31 at position 56 shown in FIG. 4a, which delimits the tangential groove portion 31c that allows the rotator 23 to rotate in the first rotational direction. By means of this engagement the plunger rod 17 will displace the rotator 23 axially. The plunger rod 17 will in particular push the rotator 23 axially. The pin member 37 will thereby move from position 49 to position 53 shown in FIG. 4b, whereby the rotator 23 will rotate a first angular distance in the first rotational direction, due to the torsional biasing. The pin member 37 will thus engage or bear against the guide surface 35b, a second guide surface or second cam surface. This corresponds to the pin member 37 being positioned at position 55 shown in FIG. 4b. The collision between the pin member 37 and the second guide surface 35b results in the second audible signal. This procedure is illustrated in FIGS. 5c and 5d. In this position, the distal end cut-out 41 of the rotator 23 has been rotated relative to the radially protruding member 43 of the end cap 11, which now bears against the distal end 45 of the rotator 23, outside the distal end cut-out 41. Furthermore, the first angular distance rotation of the rotator 23 sets the rib 33a in position 57 in the tangential groove portion 31c. The tangential groove portion 31c hence allows further rotation, in the first rotational direction, of the rotator 23 after this first angular distance rotation.

Figure 5E:
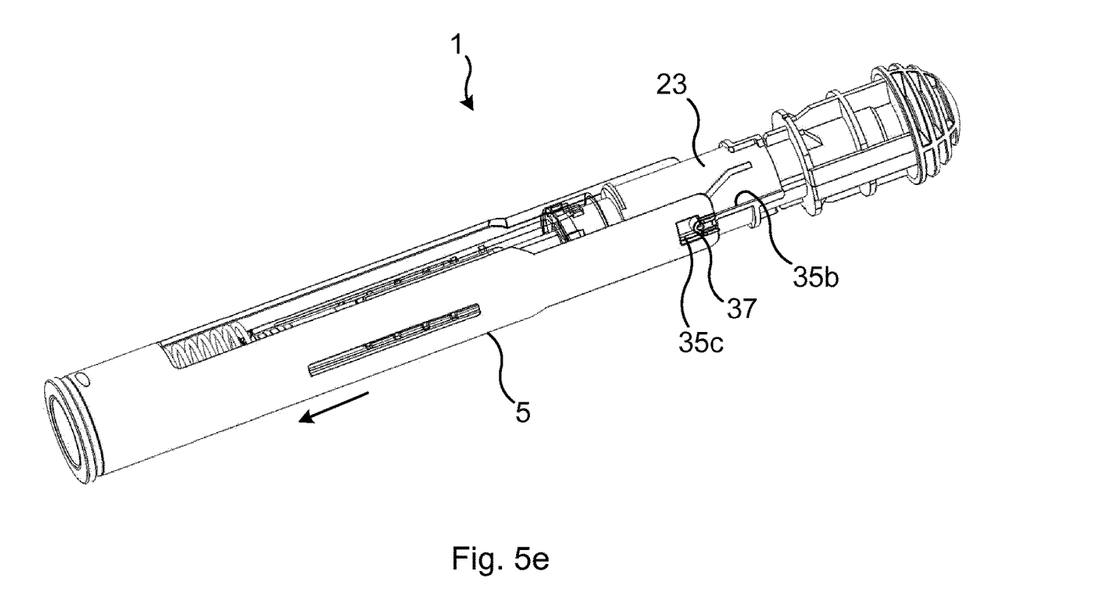

When the needle cover 5 is released from its retracted position, the needle cover 5 will return to the extended position due to its biased state. The pin member 37 will during the return motion move along the second guide surface 35b in the direction of arrow D. During this return motion, the pin member 37 will move from an elevated portion of the second guide surface 35b to a depressed portion 35c. The rotator 23 will thereby rotate a second angular distance due to the torsional biasing such that the rib 33a reaches position 60 of the tangential groove portion 31c. The pin member 37 is thus set in position 59. The interface between the elevated portion and the depressed portion is defined by a heel 35d. This heel 35d will thus prevent the needle cover 5 to be moved towards the retracted position. During this second angular distance rotation the rib 33a is moved tangentially in the tangential groove portion 31c to side wall 31e of the groove 31. The needle cover 5 is hence locked out in the extended position. This is illustrated in FIG. 5e.

During a manual resetting operation by means of the cap 7 and rod 9, the plunger rod 17 is manually pushed towards the distal end of the body 3 by the rod 9. The rib 33a is then guided along the side wall 31e of the groove 31 until it reaches a proximal end wall 31f of the tangential groove portion 31c, sloping towards the axial groove portion 31a. The rotator 23 is thereby pushed back axially and rotated in the second rotational direction as linear motion is transformed into rotational motion, such that the rib 33a becomes positioned in the axial groove portion 31a. The distal end cut-out 41 of the rotator 23 is during this rotation rotated and is able to receive the radially protruding member 43 of the end cap 11. Moreover, the rib 33a then slides along the axial groove portion 31a as the plunger rod 17 is pushed further by the rod 9. Upon reaching the tangential groove portion 31b, the rotator 23 is rotated in the first rotational direction due to the torsional biasing, and the rib 33a is positioned at position 50. Moreover, the plunger rod 17 obtains its initial plunger rod position. In this manner the medicament delivery training device 1 may be reset to be ready for additional training.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament delivery training device comprising:
   a body,
   a torsionally biased rotator received by the body, which rotator is torsionally biased in a first rotational direction, and which rotator is rotatable between a default rotator position and a final rotator position,
   an axially biased plunger rod received by the rotator, wherein in the default rotator position, the rotator is axially locked and engaged with the plunger rod to prevent axial movement of the plunger rod,
   a needle cover received by the body, axially movable and rotationally fixed relative to the body, which needle cover is movable between an extended position relative to the body and a retracted position, and which needle cover is biased towards the extended position,
   wherein the needle cover is arranged to rotate the rotator in a second rotational direction opposite to the first rotational direction during movement of the needle cover from the extended position to the retracted position, to thereby release the rotator from being axially locked and release the plunger rod from engagement with the rotator and thereby enable axial movement of the plunger rod, and
   wherein during axial movement, the plunger rod is arranged to engage with the rotator to thereby displace the rotator axially, and to allow rotation of the rotator in the first rotational direction, wherein the rotator is arranged to rotate a first angular distance, limited by the needle cover, in the first rotational direction during axial movement of the rotator, and wherein the rotator is arranged to rotate a second angular distance in the first rotational direction, into the final rotator position during return motion of the needle cover to the extended position to allow engagement with the needle cover, and thereby enable locking of the needle cover in the extended position.

2. The medicament delivery training device as claimed in claim 1, further comprising a syringe dummy, wherein in the default rotator position of the rotator, the syringe dummy is arranged to prevent the rotator from axial movement.

3. The medicament delivery training device as claimed in claim 2, wherein each of the syringe dummy and the rotator has a respective radial member arranged to abut each other in the default rotator position of the rotator.

4. The medicament delivery training device as claimed in claim 2, comprising a biased wedge member received by the plunger rod, which plunger rod has a heel arrangement protruding radially in opposite directions, wherein the wedge member is arranged to press the heel arrangement towards the inner surface of the syringe dummy.

5. The medicament delivery training device as claimed in claim 4, wherein the wedge member is biased towards a proximal end of the body.

6. The medicament delivery training device as claimed in claim 1, comprising a removable cap having a rod arranged to be received by the needle cover and arranged to reset the medicament delivery training device, wherein during insertion into the body, the rod is arranged to move the plunger rod from a final plunger rod position in which the rotator is in the final rotator position to an initial plunger rod position.

7. The medicament delivery training device as claimed in claim 6, wherein during movement of the plunger rod towards the initial plunger rod position, the plunger rod is arranged to guide the rotator into a position in which the rotator is allowed to rotate in the first rotational direction into the default rotator position.

8. The medicament delivery training device as claimed in claim 1, wherein the plunger rod is rotationally locked relative to the body.

9. The medicament delivery training device as claimed in claim 1, wherein the plunger rod and the rotator have a first guide arrangement which allows rotation of the rotator relative to the plunger rod and axial movement of the plunger rod relative to the rotator.

10. The medicament delivery training device as claimed in claim 9 wherein the first guide arrangement comprises a groove that includes an axial groove portion and one tangential groove portion at each end of the axial groove portion, and a rib arranged to engage with the groove, wherein one of the plunger rod and the rotator is provided with the groove and the other one of the plunger rod and the rotator is provided with the rib.

11. The medicament delivery training device as claimed claim 1, wherein the rotator and the needle cover have a second guide arrangement which enables rotation of the rotator and which enables locking of the needle cover in the extended position.

12. The medicament delivery training device as claimed in claim 11, wherein the second guide arrangement includes two guide surfaces and a pin member arranged to be guided by the two guide surfaces, wherein one of the rotator and the needle cover is provided with the two guide surfaces and the other one of the rotator and the needle cover is provided with the pin member.

13. The medicament delivery training device as claimed in claim 1, comprising an end cap, wherein the end cap has a radially protruding member and the rotator has a distal end cut-out, wherein the radially protruding member is arranged in the distal end cut-out in the default rotator position of the rotator, and wherein the radially protruding member is arranged to abut the distal end of the rotator, outside the distal end cut-out, in the final rotator position, to prevent axial movement of the rotator.

14. The medicament delivery training device as claimed in claim 13, wherein the rotator has a heel which in the final rotator position is arranged to prevent the needle cover to move from the extended position to the retracted position.

15. A medicament delivery training device comprising:
a body;
a torsionally biased rotator positioned in the body and torsionally biased in a first rotational direction, where the rotator is rotatable between a default rotator position and a final rotator position;
an axially biased plunger rod operatively connected to the rotator, wherein in the default rotator position, the rotator is axially locked and engaged with the plunger rod to prevent axial movement of the plunger rod;
a needle cover received by the body, axially movable and rotationally fixed relative to the body, where the needle cover is movable between an extended position relative to the body and a retracted position, and where the needle cover is biased towards the extended position; and
a syringe dummy operatively engaged with the rotator to prevent axial movement of the rotator when the rotator is in the default rotator position,
wherein the needle cover causes the rotator to rotate in a second rotational direction opposite to the first rotational direction during axial movement of the needle cover from the extended position to the retracted position, where the rotation in the second rotational direction releases the rotator from being axially locked and releases the plunger rod from engagement with the rotator to enable axial movement of the plunger rod.

16. The medicament delivery training device as claimed in claim 15, wherein the axial movement of the plunger rod engages the rotator to displace the rotator axially causing rotation of the rotator in the first rotational direction, where the rotator rotates a first angular distance followed by rotation of a second angular distance into the final rotator position during a return motion of the needle cover to the extended position and locking the needle cover in the extended position.

17. The medicament delivery training device as claimed in claim 15, further comprising a removable cap having a rod that operatively engages the needle cover to reset the medicament delivery training device by moving the plunger rod from a final plunger rod position in which the rotator is in the final rotator position to an initial plunger rod position.

18. The medicament delivery training device as claimed in claim 17, wherein during movement of the plunger rod towards the initial plunger rod position, the plunger rod guides the rotator into a position in which the rotator rotates in the first rotational direction into the default rotator position.

19. The medicament delivery training device as claimed in claim 15, wherein the plunger rod and the rotator have a first guide arrangement which allows rotation of the rotator relative to the plunger rod and axial movement of the plunger rod relative to the rotator.

20. The medicament delivery training device as claimed in claim 19, wherein the rotator and the needle cover have a second guide arrangement which enables rotation of the rotator and which enables locking of the needle cover in the extended position.

* * * * *